(12) United States Patent
Richter et al.

(10) Patent No.: US 7,618,953 B2
(45) Date of Patent: Nov. 17, 2009

(54) AMORPHOUS FORMS OF RISEDRONATE MONOSODIUM

(75) Inventors: Jindrich Richter, Pardubice (CZ); Josef Jirman, Praha 10 (CZ); Hana Petrickova, Praha 4 (CZ)

(73) Assignee: Zentiva, a.s., Praha (CZ)

( * ) Notice: Subject to any disclaimer, the term of this patent is extended or adjusted under 35 U.S.C. 154(b) by 60 days.

(21) Appl. No.: 10/590,694

(22) PCT Filed: Feb. 28, 2005

(86) PCT No.: PCT/CZ2005/000024

§ 371 (c)(1),
(2), (4) Date: Aug. 25, 2006

(87) PCT Pub. No.: WO2005/082915

PCT Pub. Date: Sep. 9, 2005

(65) Prior Publication Data

US 2007/0142332 A1 Jun. 21, 2007

(30) Foreign Application Priority Data

Feb. 26, 2004 (CZ) ................................. 2004-292
Jul. 8, 2004 (CZ) ................................. 2004-798
Aug. 12, 2004 (CZ) ................................. 2004-880

(51) Int. Cl.
*A61K 31/675* (2006.01)
*C07F 9/28* (2006.01)

(52) U.S. Cl. .......................................... 514/89; 546/22

(58) Field of Classification Search .................. 546/22; 514/89
See application file for complete search history.

(56) References Cited

U.S. PATENT DOCUMENTS 6,410,520 B2 * 6/2002 Cazer et al. ..................... 514/89
2005/0215793 A1 * 9/2005 Turchetta et al. ............... 546/22

2006/0148762 A1 7/2006 Richter et al.

FOREIGN PATENT DOCUMENTS

WO 98 57967 12/1998
WO 01 56983 8/2001

OTHER PUBLICATIONS

Brittain et al., Polymorphism in Pharmaceutical Sciences, NY:Marcel Dekker pp. 1-2, 183-226).*
Threifall et al., "Analysis of Organic, etc.," Analyst, 1995, 120, 2435-2460.*
Muzaffar et al., "Polymorphism and Drug, etc.," J of Pharmacy (Lahore). 1979, 1(1), 59-66.*
Doelker, english translation of S.T.P. Pharma Pratiques (1999), 9(5), 299-409, pp. 1-33.*
Xu ,"An easy and primary, etc.," J of Zhejiang University of Technology, 31 (4), 2003, 456-459.*
Lester et al., "Dehydration of, etc.," J of Pharmaceutical Sciences, 95 (12), 2006, 2631-2644.*
Singhal et al., "Drug Polymorphism, etc.," Advanced Drug Delivery Reviews 56 (2004) 335-347.*
U.S. Pharmacopia #23, National Formulary # 18 (1995) 1843-1844.*
Bernstein et al., "Polymorphism in, etc.," Oxford: Clarendon Press, 2002, pp. 117,118,272 and 273.*
Davidovich et al., "Detection of, etc.," American Pharmaceutical Review, IN: Russell Pub., 2004, 7(1), pp. 10,12,14,16 and 100.*
Mehta, Surendra C.,"Issues and Approaches for Improving the Solubiliti and Bioavailability of Poorly Water Soluble Compounds", Bulletin Technique Gattefosse Report, vol. 91, No. 91, pp. 65-72, 1998.

* cited by examiner

*Primary Examiner*—Patricia L Morris
(74) *Attorney, Agent, or Firm*—Oblon, Spivak, McClelland, Maier & Neustadt, L.L.P.

(57) ABSTRACT

The monosodium salt of 3-pyridyl-1-hydroxyethylidene-1,1-bisphosphonic acid in new amorphous forms, methods of preparation and a pharmaceutical formulation.

19 Claims, 9 Drawing Sheets

AMORPHOUS FORMS OF RISEDRONATE MONOSODIUM

TECHNICAL FIELD

The invention concerns new amorphous forms of the monosodium salt of 3-pyridyl-1-hydroxyethylidene-1,1-bisphosphonic acid (formula I)

and methods for preparing the same.

BACKGROUND ART

Geminal bisphosphonates, such as for example salts of 3-pyridyl-1-hydroxyethylidene-1,1-bisphosphonic acid (RISEDRONATE) or 4-amino-1-hydroxybutylidene-1,1-bisphosphonic acid (ALENDRONATE) have been used for already some time to treat bone diseases and for management of the metabolism of calcium.

Preparation of risedronic acid consists in the reaction of 3-pyridylacetic acid with phosphorous acid and phosphorus trichloride and subsequent hydrolysis of the resulting intermediates. A general method of this preparation of bisphosphonic acids was presented in JP 80-98193 (1980), JP 80-98105 (1980) of Nissan Chemical Industries and in the article of W. Ploger et al., Z. Anorg. Allg. Chem., 389, 119 (1972). Preparation of risedronate was presented in EP 186405 (1986) of Procter & Gamble.

Bisphosphonic acids are used in the form of various non-toxic and pharmaceutically acceptable esters, salts of alkali metals and alkaline-earth metals and their various hydrates. The form of the substance can have fundamental influence on its solubility and biological availability. The sodium and calcium salts are the preferred forms of risedronate.

3-pyridyl-1-hydroxyethylidene-1,1-bisphosphonic acid is used especially in the form of its monosodium salt (SODIUM RISEDRONATE). This salt, like a number of geminal bisphosphonic acids and their salts, can form hydrates. So far, anhydrous crystalline form of monosodium 3-pyridyl-1-hydroxyethylidene-1,1-bisphosphonate, its monohydrate and pentahemihydrate have been described, namely in Procter & Gamble's application WO 01/56983 A2. Of the two mentioned hydrates, only the pentahemihydrate form is thermodynamically stable. The monohydrate spontaneously transforms to the stable pentahemihydrate.

The pentahemihydrate is prepared by forming a suspension of risedronic acid in water at about 60° C., adjusting the pH of the suspension to 4.5 to 5 with sodium hydroxide, adding isopropanol to the resulting solution at the same temperature, and gradually cooling the resulting suspension. The temperature of formation of first crystals is important for producing pure pentahemihydrate, which is most preferably maintained at between 50 to 70° C.

The monohydrate containing formulation, described in application WO 01/56983, therefore, necessarily absorbs water from the environment and changes its composition. This can be a significant source of instability of this form.

CZ patent 293349 (WO 2004/037252) describes higher hydrates of the monosodium, di-sodium and tri-sodium salts of 3-pyridyl-1-hydroxyethylidene-1,1-bisphosphonic acid. It has turned out that these salts do not take in any additional water from the air and it can be assumed that a composition comprising them will be more stable than that comprising the earlier-described mixture of the monosodium salt mono- and pentahemihydrates. The pentahydrate form of the monosodium salt is described therein, inter alia. The pentahydrate is one of alternative solutions to the earlier-described hemipentahydrate. It is stable especially in the wet environment. This hydrate was prepared from a solution of the monosodium salt in water, which is poured at 80° C. into isopropanol, cooled to −7 to −10° C.

Another solution is described in patent application WO 03/086355. The structure of the earlier-known hemipentahydrate was designated as polymorph A therein. The new crystalline form B, disclosed in this application, is the monohydrate; contrary to the earlier-known monohydrate, it is stable at normal conditions. In the invention, further crystalline forms C through H are also defined.

Methods of preparation of individual forms consist either in boiling a suspension of risedronic acid in a solution of sodium hydroxide in a mixture water-organic solvent, or in heating the monosodium salt to 100 to 200° C., or in exposing the salt to wet atmosphere for longer periods of time.

All forms of the monosodium salt of risedronic acid, described so far, have been crystalline. However, it turns out in many cases relating to pharmaceutically active substances that an amorphous form is biologically more available. Because biological availability of salts of bisphosphonic acids is generally very low—the organism usually makes use of about 1% of the total mass of the used active substance—it is desirable to find such forms that would have a larger utilizable portion.

The present invention, therefore, concerns new amorphous forms of the monosodium salt of risedronic acid (or risedronate sodium).

DISCLOSURE OF INVENTION

The substance to which this invention relates—amorphous monosodium salt of risedronic acid—is termed amorphous risedronate throughout the specification.

The amorphous forms are well characterized by the X-ray diffraction pattern, where one cannot observe any characteristics of the crystalline phase in the form of sharp maximums. The $^{13}$C and $^{31}$P of CP MAS NMR spectra and Raman spectra show observable expanded lines, caused by non-existence of preferential orientation of molecules in the amorphous form. The substance according to the invention is characterized especially by bands at 3084, 2936, 1633, 1051 and 120 cm$^{-1}$ in the Raman spectrum and expanded bands at 139, 125, 75 and 37 ppm in the $^{13}$C CP MAS NMR spectrum.

The amorphous form can be prepared by heating crystalline risedronate, especially risedronate pentahydrate, at a temperature above 60° C. for several hours, especially at 60 to 200° C. for 1 to 48 hours. It is preferable to heat up at 100 to 140° C., more preferably at 130° C.

The amorphous forms of the invention include also forms that can be designated as semi-crystalline. The semi-crystalline form of the invention can be characterized as a virtually amorphous substance, i.e., that for which no crystal lattice is defined. For the semi-crystalline form, however, larger or smaller symptoms of an arrangement can be identified by methods of structural analysis. Given that usual methods can determine an admixture of a crystalline phase in concentrations of 2 to 5%, it is obvious that the semi-crystalline form contains, if any, only a small amount of a crystalline phase. The intensities of isolated peaks, measured by the method of X-ray diffraction, would, however, correspond to a substantially larger fraction. The semi-crystalline form cannot therefore be characterized otherwise than as an amorph with symptoms of arrangement in a certain direction, i.e. not in the three-dimensional crystal lattice.

This form is well characterized by the X-ray diffraction pattern, where one can observe two sharp characteristic peaks at angles of 5.85 and 6.99° 2θ; moreover, this form is characteristic by a very broad band at 17.6° 2θ and a plateau (without peaks) between 23-35° 2θ. In the $^{13}$C and $^{31}$P of CP MAS NMR spectra and IR spectra there can be observed expanded lines, caused by non-existence of preferential orientation of molecules in the semi-crystalline form. The substance according to the invention is characterized especially by expanded bands at 3085, 2786, 2379, 1561, 1212 and 809 cm$^{-1}$ in the IR spectrum and expanded bands at 137.9, 124.5, 73.6, 36.8 ppm in the $^{13}$C CP MAS NMR spectrum.

The semi-crystalline form can be prepared by heating crystalline risedronate pentahydrate at a temperature above 60° C. for several hours, especially at 60 to 200° C. for 1 to 48 hours. It is preferable to heat up at 100 to 140° C., more preferably at 110° C.

It has turned out that the above described amorphous forms of risedronate according to this invention are stable at normal conditions and are suitable for preparation of pharmaceutical formulations. The amorphous forms of risedronate can contain 0 to 7% of water. In a preferred embodiment the water content is 4 to 7%, where the substance is more stable also in the wet environment.

In an advantageous manner, the amorphous form of the invention can be prepared by spray drying a solution of risedronate sodium, or a solution of risedronate sodium in a mixed solvent wherein one of the components is water and the second one is a C1 to C4 alcohol, in a gas stream. The solution may contain 1 to 250 g/l of risedronate sodium.

Drying can be carried out at temperatures in the range of 50° C. to 200° C. Higher temperatures during drying are not detrimental and do not cause decomposition of the substance being dried, since the solution is exposed thereto for only a short period of time. In preparation of the amorphous form by drying the crystalline pentahydrate at higher temperatures partial decomposition occurs.

The feed nozzle of the drier can have a temperature of 70 to 220° C. and the gas outlet from the drier can have a temperature of 40 to 150° C.; preferably the temperature is maintained at 50 to 70° C.

Thus prepared amorphous form of risedronate can contain 0 to 10% by weight of water. In a preferred embodiment it contains 7 to 10% by weight of water, more preferably 9 to 10% by weight of water, where the substance is more stable also in the wet environment.

For the amorphous risedronate having the higher water content it has been surprisingly found out that it can be prepared in the solid state and that it does not transform to the crystalline form upon storing. These amorphous risedronates having the higher water content have the advantage of not being hygroscopic, thus avoiding necessity of being stored without access of air humidity.

The content of water in the amorphous forms of risedronate sodium is determined by the TGA method and it depends on the length and temperature of drying and the solvent used and it does not have any influence on changes of the characteristic spectra of the substance.

Another aspect of the invention includes a pharmaceutical formulation containing amorphous risedronate.

Preferred forms for utilization of amorphous risedronate are oral formulations, especially in the form of tablets. Besides the active substance, suitable diluents, binders, disintegrants and glidants are used to prepare the tablet.

A composition that can be directly compressed is an extraordinarily advantageous combination, where a mixture of mannitol and microcrystalline cellulose plays the role of the diluent. This combination displays exceptional stability, especially in the wet environment.

A dosage form can contain 5 to 35 mg of the active substance, based on pure risedronic acid. Forms of 5 mg for once-a-day administration and 35 mg for once-a-week administration are the preferable ones.

Bisphosphonic acids such as alendronate or risedronate are known to have very low biological availability. Usually, less than 2% of the administered amount of the substance can be utilized by the organism.

Poor bioavailability is often caused by insufficient speed of dissolution of the substance in liquids, i.e. in diluted hydrochloric acid (pH about 1.2), critical for dissolution in the stomach, or in water (at pH about 6), critical for dissolution in the small intestine.

Dissolution of risedronate sodium in HCl occurs, when this active substance is in a common tablet, which disintegrates and dissolves in the patient's stomach. The second type of dissolution is characteristic for a tablet having and acid-resistant coating, which is described for sodium risedronate in WO 93/09785 and which passes the stomach as a whole and disintegrates only in the neutral pH of the small intestine, wherein the active substance first dissolves.

A comparison of both types of dissolution for known sodium risedronate pentahemihydrate according to WO 01/56983 and for sodium risedronate prepared according to Example 2 of this application is made in examples 10 and 11 below.

Bisphosphonates are always administered to patients when fasting, i.e. before foods; the preparation Actonel (sodium risedronate active substance) is to be administered at least 30 mins before the first daily meal. In these circumstances, residence of the medicament in the stomach lasts only several minutes. It follows from the results of Example 10 below that while risedronate according to this invention would remain in the solution in the stomach and would pass to the small intestine, wherein it would be absorbed into blood, risedronate administered in the usual form of pentahemihydrate would partly or wholly precipitate from the stomach juices and would leave the stomach in the form of a precipitate. A tablet containing the risedronate according to this invention, hence, has conditions for the active substance to pass into blood in a greater amount, which would improve total bioavailability.

It follows from the results of Example 11 below that if sodium risedronate were administered in an acid-resistant coating, the tablet would enter the small intestine as a whole, wherein it would and the active substance would dissolve and be absorbed in the form of the sodium salt. In this case, too, the active substance in the form of this invention would dissolve more faster than that of the prior art and it would have a longer period for being absorbed.

As a conclusion, sodium risedronate according to this invention will be dissolved for a longer period in the digestion process, which indicates a better bioavailability than that of sodium risedronate in the form of pentahemihydrate.

EXAMPLES

Example 1

Figure 1:
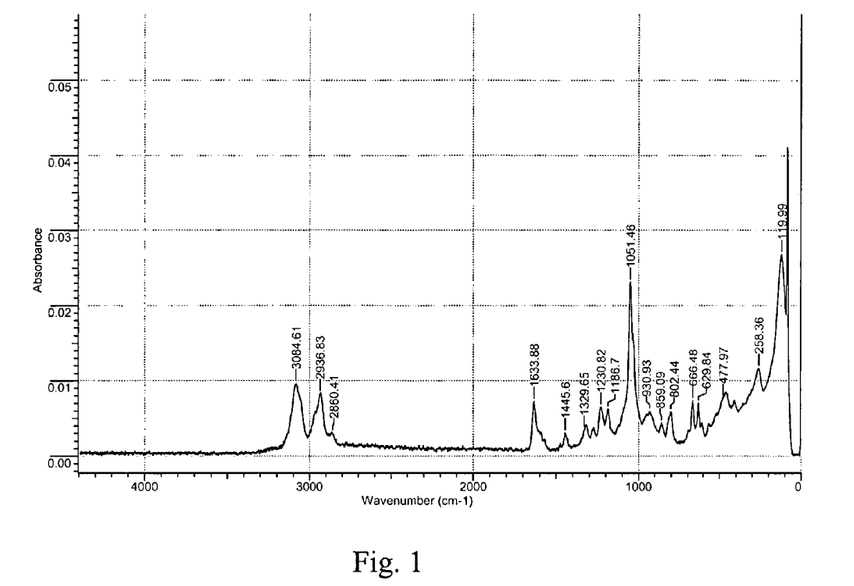
FIG. 1 presents the Raman spectrum of amorphous risedronate prepared according to Example 1.
Figure 2:
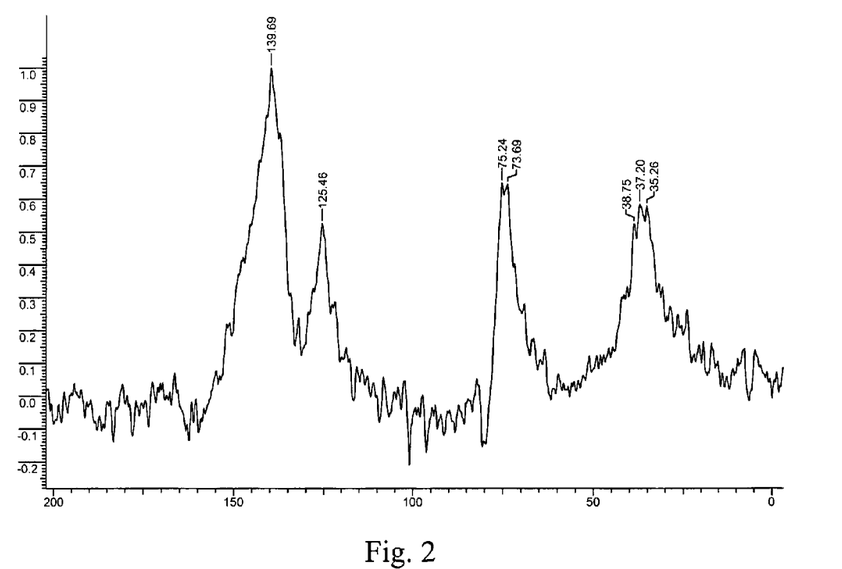
FIG. 2 presents the $^{13}$C CP MAS NMR spectrum of amorphous risedronate prepared according to Example 1.
Figure 3:
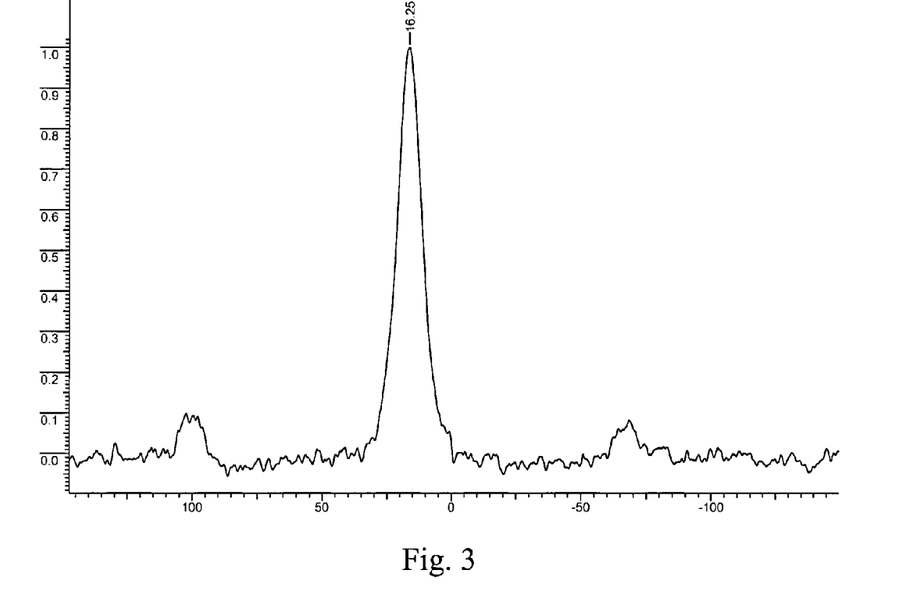
FIG. 3 presents the $^{31}$P CP MAS NMR spectrum of amorphous risedronate prepared according to Example 1.
Figure 4:
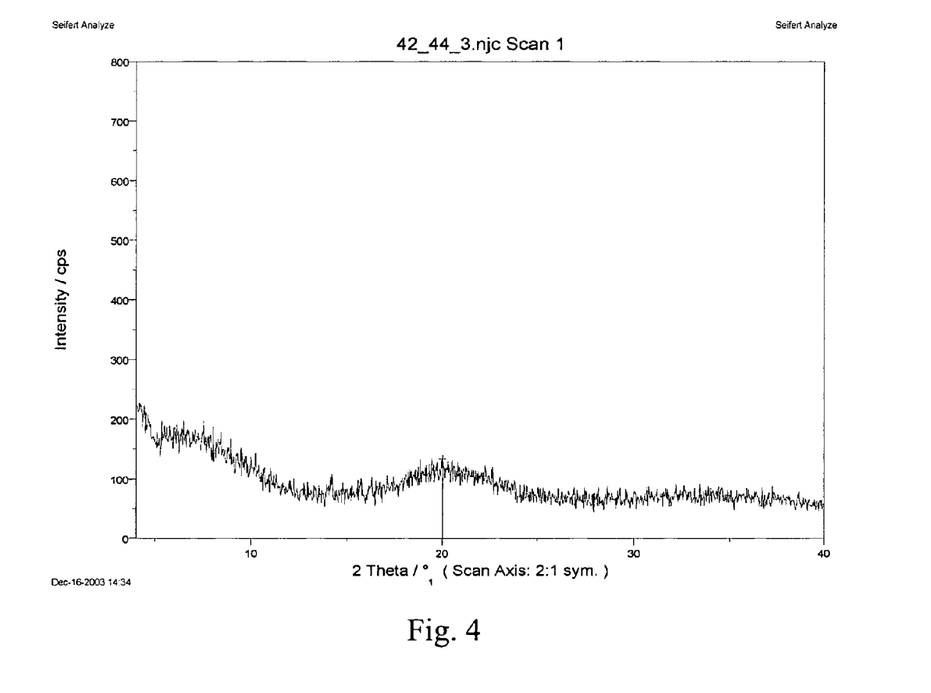
FIG. 4 presents the X-ray diffraction pattern of amorphous risedronate prepared according to Example 1.
Figure 5:
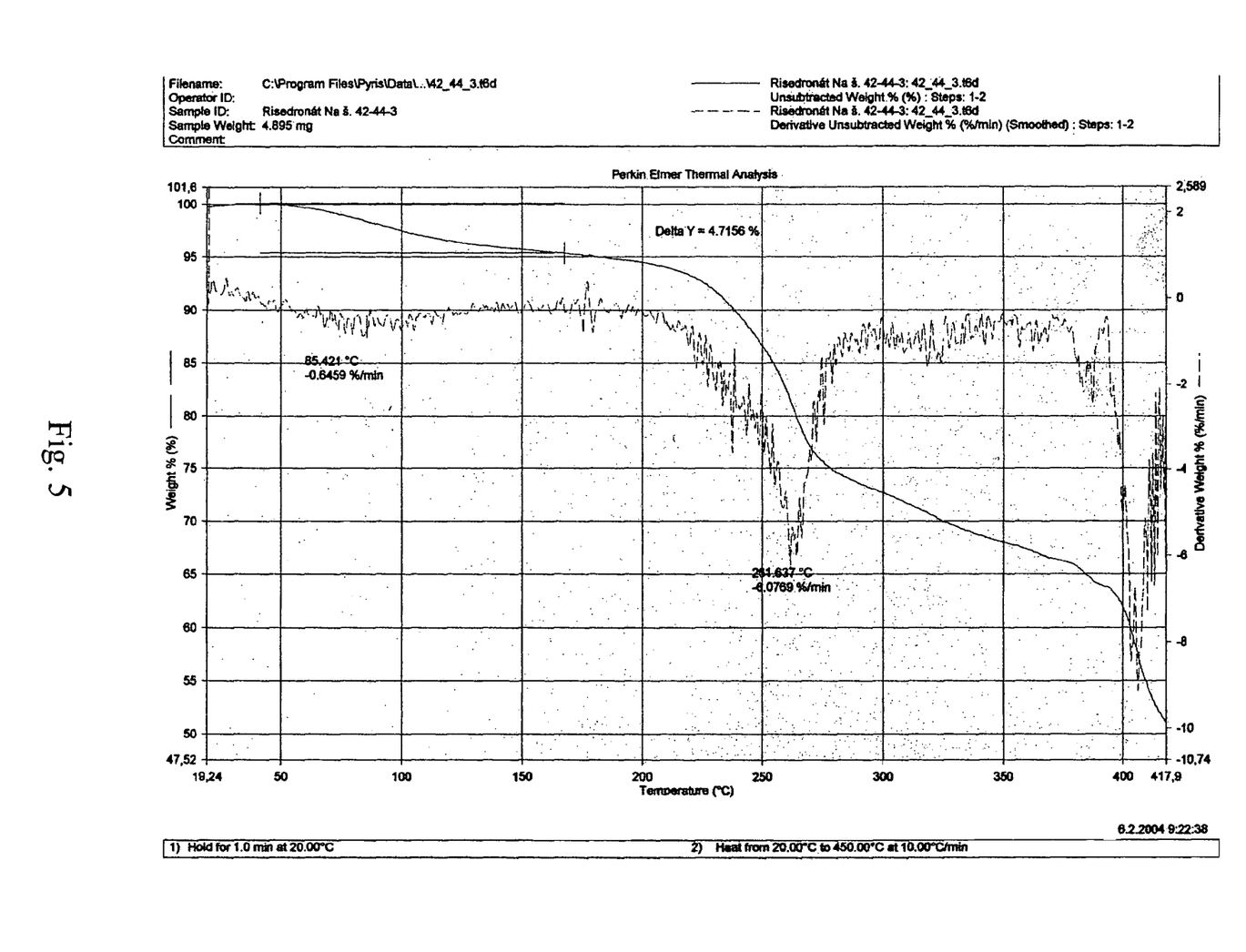
FIG. 5 presents the result of thermogravimetric analysis of amorphous risedronate prepared according to Example 1.

A Method of Preparation of the Amorphous Form of Risedronate Sodium:

10 g of crystalline form of risedronate pentahydrate (according to WO 2004/037252) was dried at 130° C. for 5 hours. 8.46 g of the amorphous form of risedronate sodium was obtained, which was characterized with X-ray powder diffraction (FIG. 4), $^{13}$C and $^{31}$P Cp MAS NMR spectra (FIGS. 2 and 3) and Raman spectra (FIG. 1) and TGA (thermogravimetric analysis) (FIG. 5), according to which the prepared amorphous risedronate contained 4.7% of water.

Example 2

Figure 6:
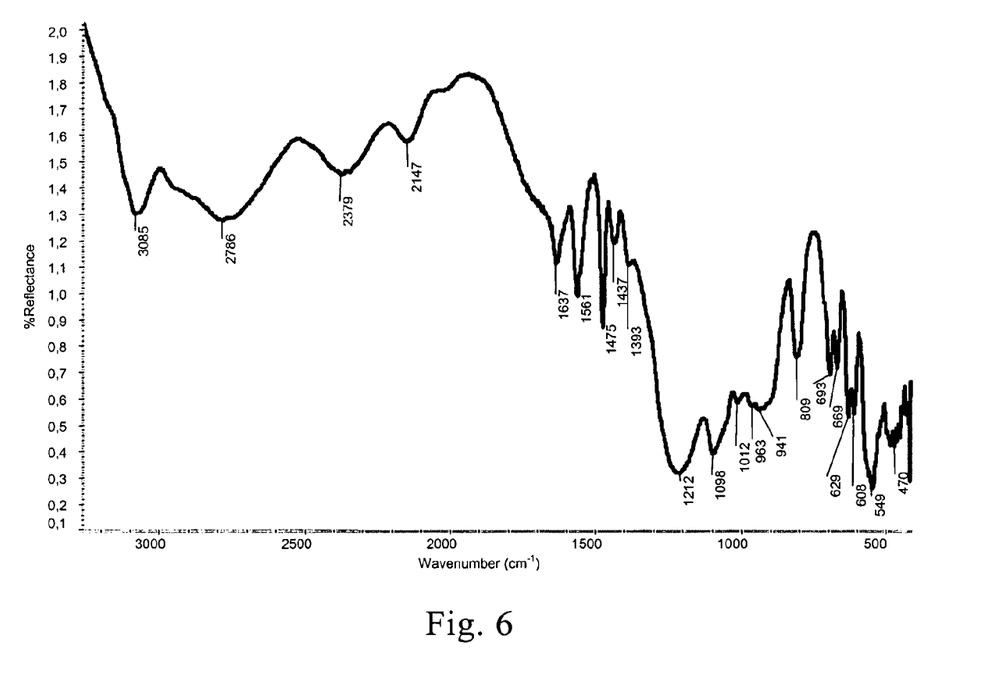
FIG. 6 presents the IR spectrum of semi-crystalline risedronate prepared according to Example 2.
Figure 7:
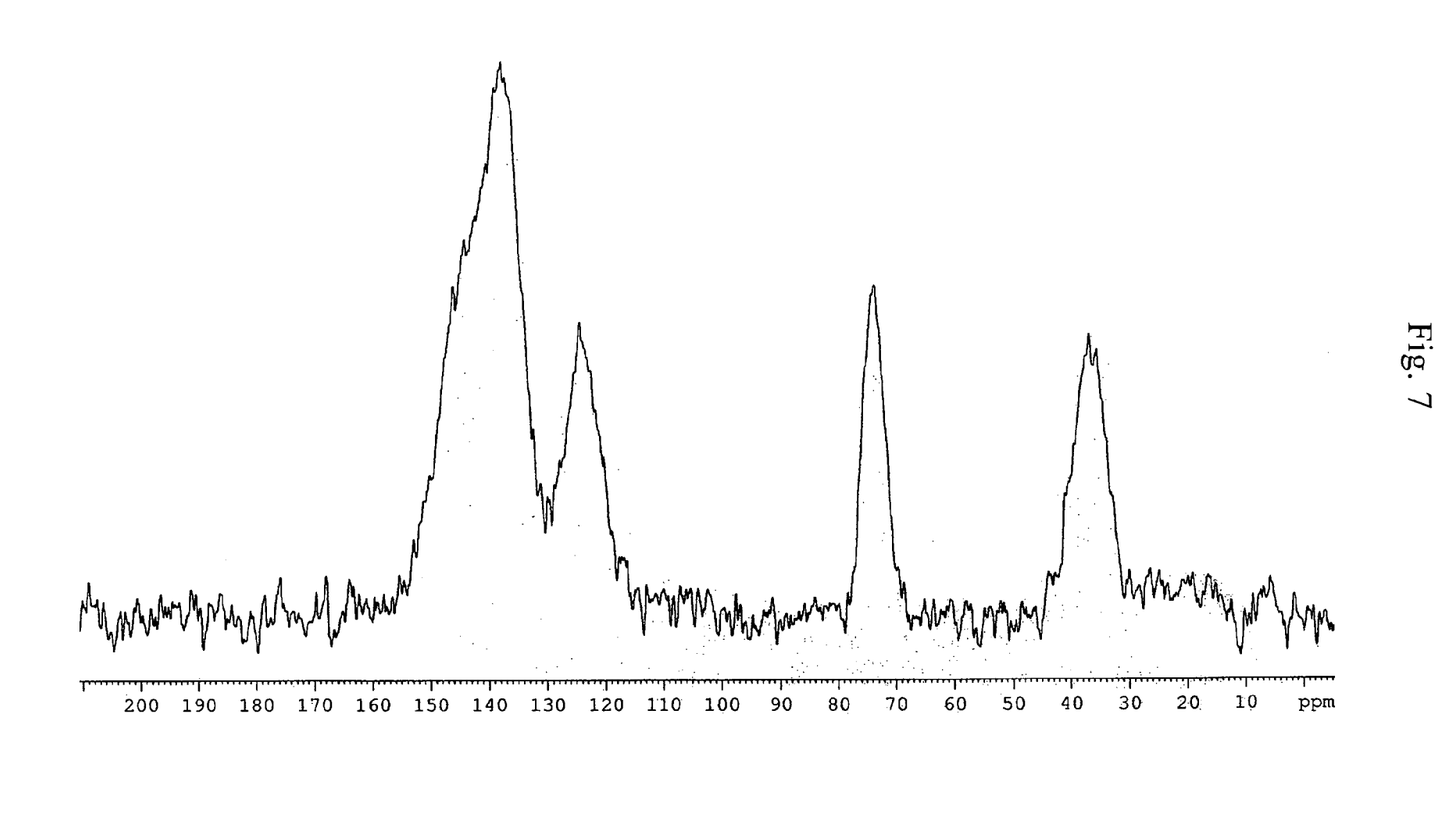
FIG. 7 presents the $^{13}$C CP MAS NMR spectrum of semi-crystalline risedronate prepared according to Example 2.
Figure 8:
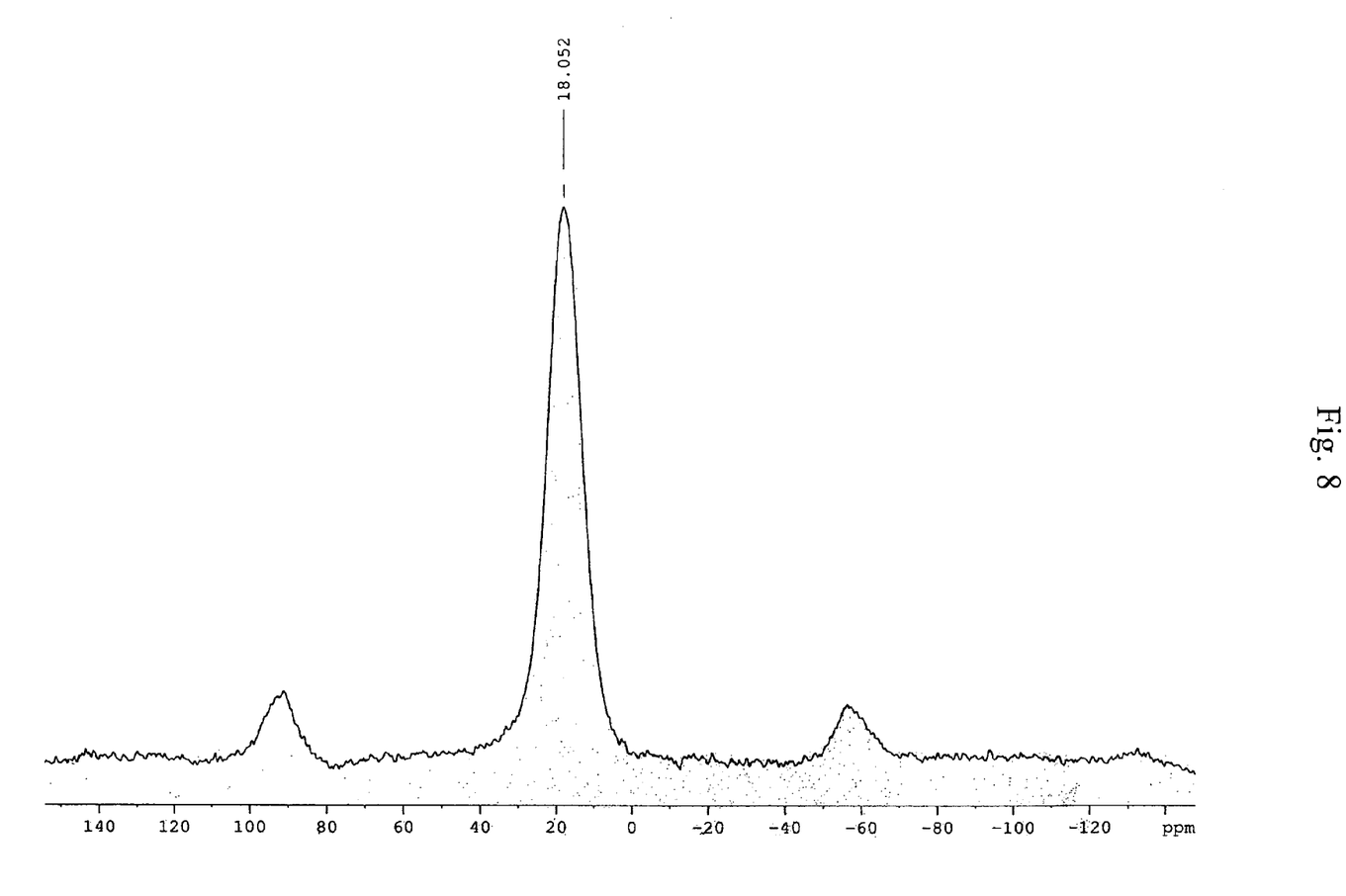
FIG. 8 presents the $^{31}$P CP MAS NMR spectrum of semi-crystalline risedronate prepared according to Example 2.
Figure 9:
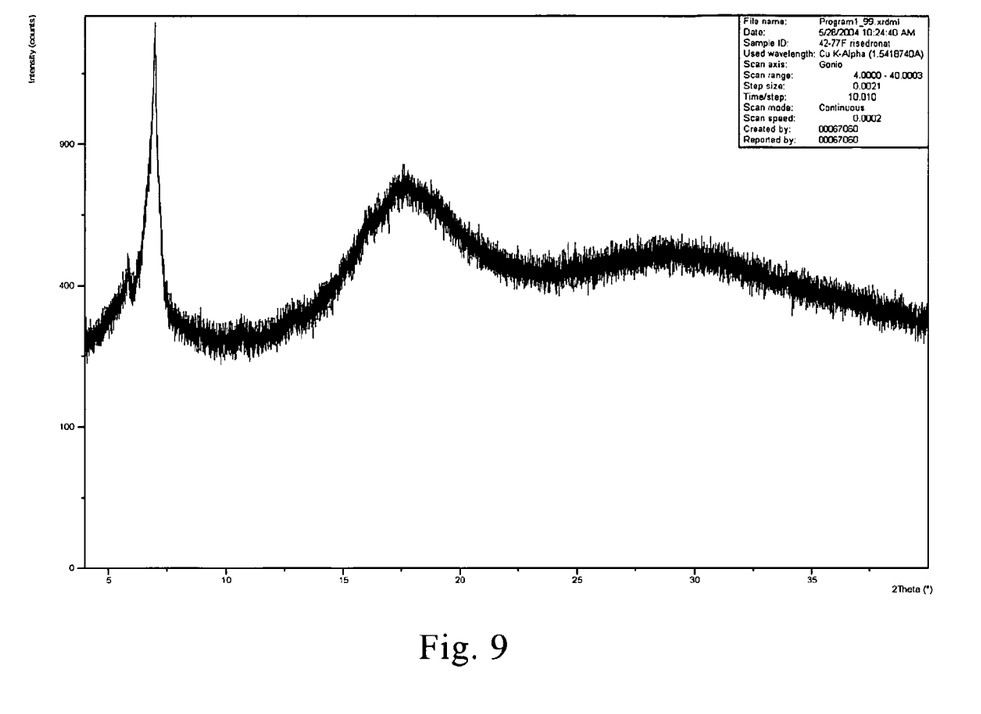
FIG. 9 presents the X-ray diffraction pattern of semi-crystalline risedronate prepared according to Example 2.
Figure 10:
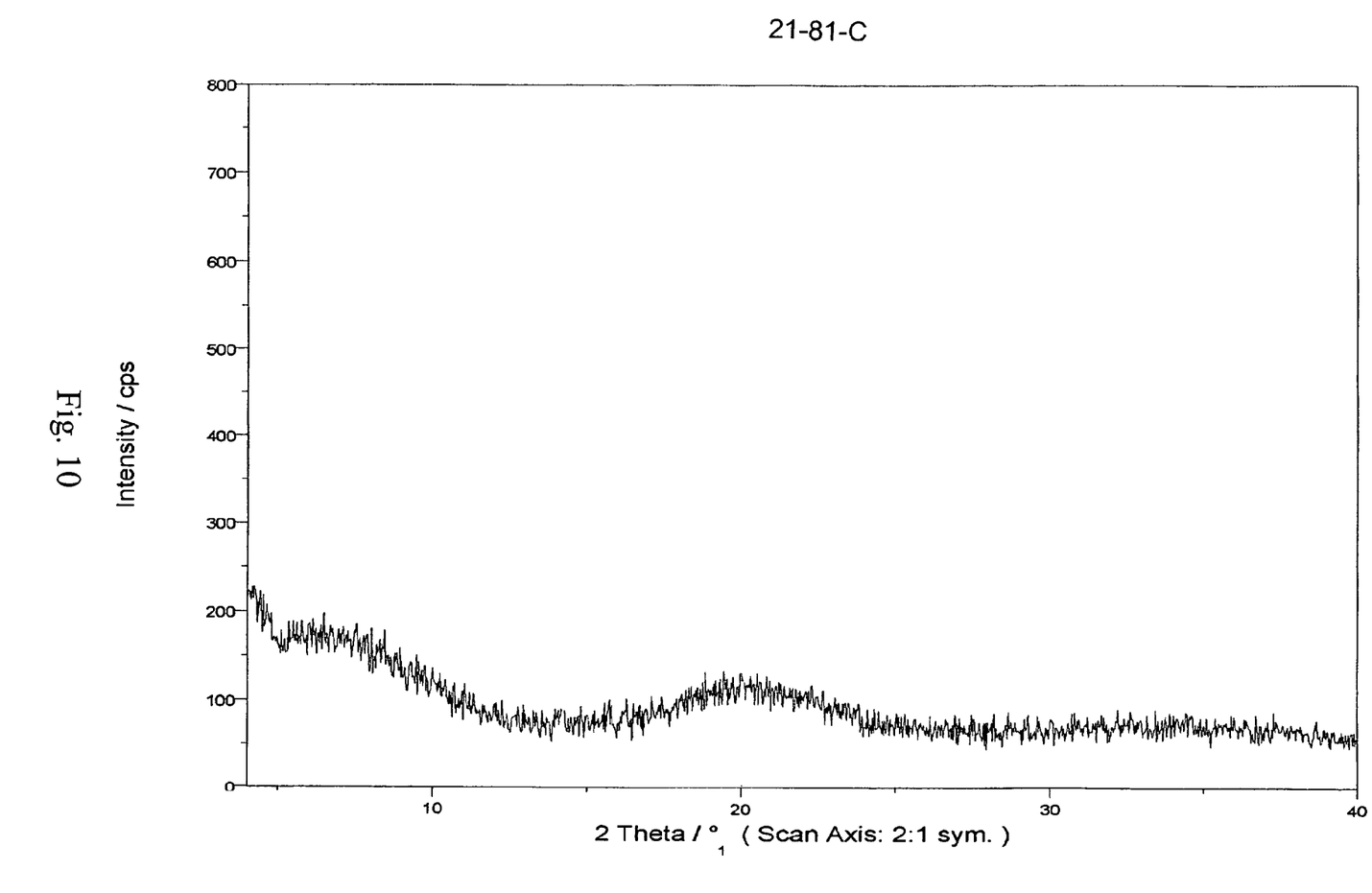
FIG. 10 presents the X-ray diffraction pattern of amorphous risedronate prepared according to Example 5.
Figure 11:
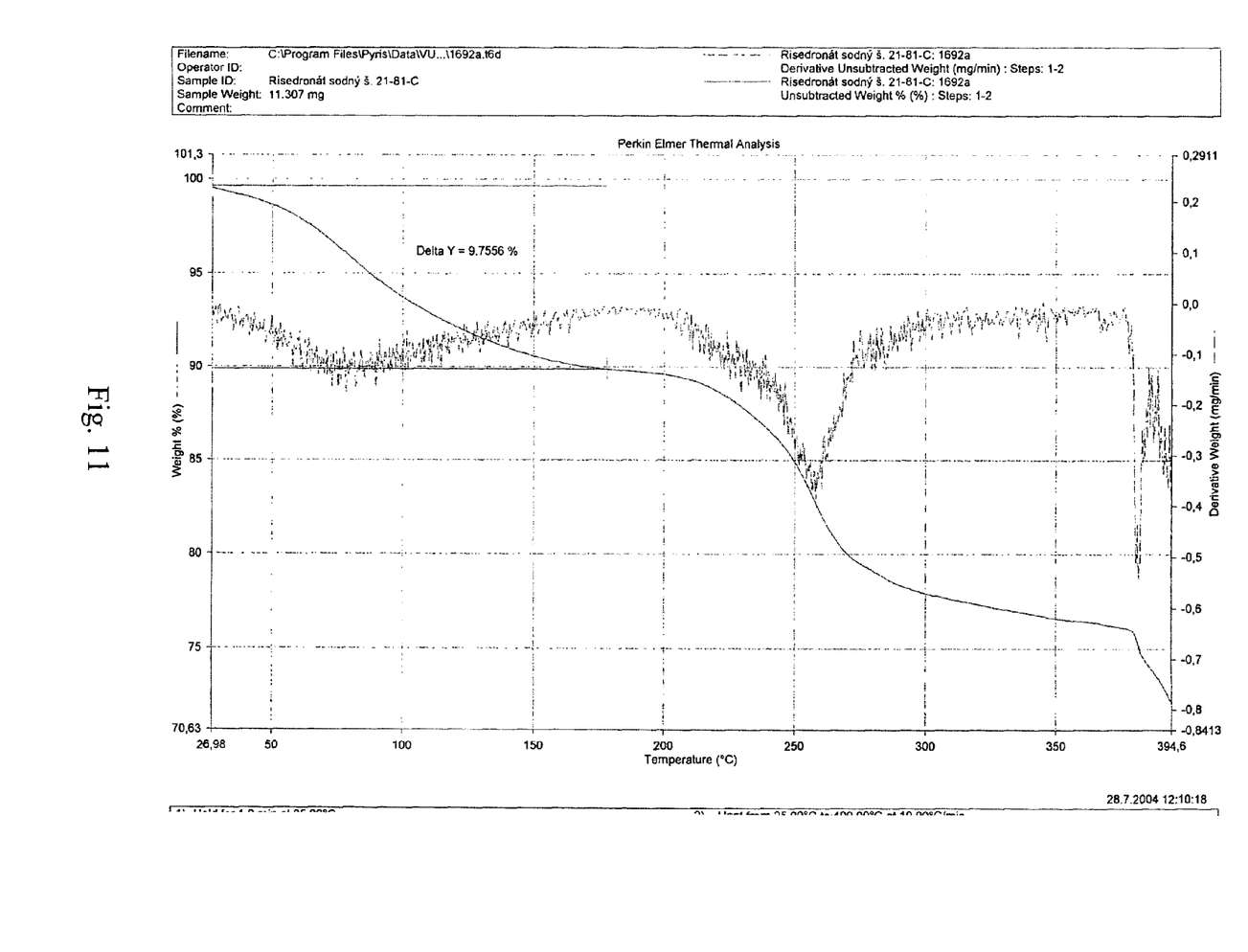
FIG. 11 presents the result of thermogravimetric analysis of amorphous risedronate prepared according to Example 5.

A Procedure of Preparation of the Semi-Crystalline Form of Risedronate Sodium:

10 g of crystalline form of risedronate pentahydrate (according to WO 2004/037252) was dried at 110° C. for 20 hours. 8.2 g of the semi-crystalline form of risedronate sodium was obtained, which was characterized with X-ray powder diffraction (FIG. 9), $^{13}$C and $^{31}$P Cp MAS NMR spectra (FIGS. 7 and 8) and IR spectra (FIG. 6). Thus prepared semi-crystalline risedronate contained 1.7% of water. After one month storage on the open air at laboratory temperature the content of water increased to 3%.

Example 3

A Procedure of Preparation of the Semi-Crystalline Form of Risedronate Sodium:

10 g of crystalline form of risedronate pentahydrate (according to WO 2004/037252) was dried at 50° C. for 5 hours, then the temperature was elevated to 100° C. and drying was continued for 10 hours. 8.5 g of the semi-crystalline form of risedronate sodium was obtained, which was characterized with X-ray powder diffraction, $^{13}$C and $^{31}$P CP MAS NMR spectra and IR spectra. Thus prepared semi-crystalline risedronate contained 1.5% of water.

Example 4

A Procedure of Preparation of the Semi-Crystalline Form of Risedronate Sodium:

10 g of crystalline form of risedronate pentahydrate (according to WO 2004/037252) was dried under pressure of 10-30 kPa at 100° C. for 10 hours. 8.1 g of the semi-crystalline form of risedronate sodium was obtained, which was characterized with X-ray powder diffraction, $^{13}$C and $^{31}$P Cp MAS NMR spectra and IR spectra. Thus prepared semi-crystalline risedronate contained 0.8% of water.

Example 5

A Procedure of Preparation of the Amorphous Form of Risedronate Sodium:

A solution of risedronate sodium in a mixture of 30% of methanol and 70% of water having the concentration 36 $g*l^{-1}$ and temperature 25° C. was continuously fed into a spray drier with concurrent stream of nitrogen. The feed temperature was 100° C. and that of the cyclone outlet was 50° C. 90% of amorphous risedronate sodium was obtained in this manner (the remainder was contained in the outlet filter of the drier). Thus prepared amorphous risedronate contained 9.7% by weight of water.

Example 6

A solution of risedronate sodium in a mixture of 20% of ethanol and 80% of water having the concentration 40 $g*l^{-1}$ and temperature 40° C. was continuously fed into a spray drier with concurrent stream of nitrogen. The feed temperature was 100° C. and that of the cyclone outlet was 52° C. 93% of amorphous risedronate sodium was obtained in this manner (the remainder was contained in the outlet filter of the drier). Thus prepared amorphous risedronate contained 9.3% by weight of water.

Example 7

A solution of risedronate sodium in a mixture of 30% of isopropanol and 70% of water having the concentration 36 $g*l^{-1}$ and temperature 25° C. was continuously fed into a spray drier with concurrent stream of nitrogen. The feed temperature was 100° C. and that of the cyclone outlet was 54° C. 90% of amorphous risedronate sodium was obtained in this manner (the remainder was contained in the outlet filter). Thus prepared amorphous risedronate contained 8% by weight of water.

Example 8

A solution of risedronate sodium in water having the concentration 50 $g*l^{-1}$ and temperature 25° C. was continuously fed into a spray drier with concurrent stream of nitrogen. The feed temperature was 150° C. and that of the cyclone outlet was 60° C. 90% of amorphous risedronate sodium was obtained in this manner (the remainder was contained in the outlet filter). Thus prepared amorphous risedronate contained 7.8% by weight of water.

Example 9

A solution of risedronate sodium in water having the concentration 200 $g*l^{-1}$ and temperature 60° C. was continuously fed into a spray drier with concurrent stream of nitrogen. The feed temperature was 200° C. and that of the cyclone outlet was 120° C. 89% of amorphous risedronate sodium was obtained in this manner (the remainder was contained in the outlet filter). Thus prepared amorphous risedronate contained 0.7% by weight of water.

Example 10

Dissolution of Sodium Risedronate in Diluted Hydrochloric Acid a) 0.273 g (0.796 mmol) of sodium risedronate pentahemihydrate (crystalline form A) according to WO 01/56983, having the water content 12.5%, was introduced into 100 ml of stirred aqueous solution of hydrochloric acid at pH 1.1 and temperature of 40° C. Within 30 seconds a transparent solution was formed. However, within additional 20 seconds, a white suspension of poorly soluble risedronic acid started to precipitate and did not dissolve even upon further stirring in constant conditions.

b) 0.250 g (0,796 mmol) of semi-crystalline sodium risedronate according to Example 2 above, having the water content 3%, was introduced into 100 ml of stirred aqueous solution of hydrochloric acid at pH 1.1 and temperature of 40° C. Within less than 30 seconds a quite transparent solution was formed. It was stirred for further 15 mins under constant conditions without any observable precipitation.

Example 11

Dissolution of Sodium Risedronate in Water a) 0.200 g (0.583 mmol) of sodium risedronate pentahemihydrate (crystalline form A) according to WO 01/56983, having the water content 12.5%, was suspended in 2 ml of water at 22° C. Water was added dropwise to the stirred suspension at 0.2 ml/min until a transparent solution was formed. The total consumption of water for dissolution of the sample was 3.5 ml.

b) 0.200 g (0,637 mmol) of semi-crystalline sodium risedronate according to Example 2 above, having the water content 3%, was suspended in 2 ml of water at 22° C. Water was added dropwise to the stirred suspension at 0.2 ml/min until a transparent solution was formed. The total consumption of water for dissolution of the sample was 2.5 ml.

The above comparison experiment shows that solubility of sodium risedronate according to this invention in water is higher since the molar concentration of 0.255 mol/l can be quickly achieved. For the crystalline form A, only the concentration of 0.167 mol/l was achieved within the same period.

The invention claimed is:

1. The monosodium salt of 3-pyridyl-1-hydroxyethylidene-1,1-bisphosphonic acid in an amorphous form, having the X-ray diffraction pattern showing a characteristic broad obtuse peak at 2θ angles ranging from 15 to 25°, and, optionally, two sharp peaks at 2θ angles of 5.856 and 6.99°.

2. The monosodium salt of 3-pyridyl-1-hydroxyethylidene-1,1-bisphosphonic acid in an amorphous form according to claim 1, having a characteristic broad obtuse peak at 2θ angles ranging from 17.4 to 20.2°.

3. The monosodium salt of 3-pyridyl-1-hydroxyethylidene-1,1-bisphosphonic acid in an amorphous form according to claim 1, having bands at 3084, 2936, 1633, 1051 and 120 cm$^{-1}$ in the Raman spectrum and expanded bands at 139, 125, 75 and 37 ppm in the $^{13}$C CP MAS NMR spectrum.

4. The monosodium salt of 3-pyridyl-1-hydroxyethylidene-1,1-bisphosphonic acid in an amorphous form according to claim 1, having two sharp peaks at 2θ angles of 5.856 and 6.99°, a broad band at 2θ 17.6°, and a plateau without peaks between 2θ angles of 23-35°.

5. The monosodium salt of 3-pyridyl-1-hydroxyethylidene-1,1-bisphosphonic acid in an amorphous form according to claim 4, having expanded bands at 3085, 2786, 2379, 1561, 1212 and 809 cm$^{-1}$ in the IR spectrum and expanded bands at 137.9, 124.5, 73.6, 36.8 ppm in the $^{13}$C CP MAS NMR spectrum.

6. The monosodium salt of 3-pyridyl-1-hydroxyethylidene-1,1-bisphosphonic acid in an amorphous form according to claim 3, having the water content of 0 to 7% by weight.

7. The monosodium salt of 3-pyridyl-1-hydroxyethylidene-1,1-bisphosphonic acid in an amorphous form according to claim 6, having the water content of 4 to 7% by weight.

8. The monosodium salt of 3-pyridyl-1-hydroxyethylidene-1,1-bisphosphonic acid in an amorphous form according to claim 3, having the water content of 7 to 10% by weight.

9. The monosodium salt of 3-pyridyl-11hydroxyethylidene-1,1-bisphosphonic acid in an amorphous form according to claim 8, having the water content of 9 to 10% by weight.

10. A method of preparing the monosodium salt of 3-pyridyl-1-hydroxyethylidene-1,1-bisphosphonic acid in an amorphous form having two sharp peaks at 2θ angles of 5.856 and 6.99°, a broad band at 2θ 17.6°, and a plateau without peaks between 2θ angles of 23-35°, wherein the method comprises heating the monosodium salt of 3-pyridyl-1-hydroxyethylidene-1,1-bisphosphonic acid of formula I in the crystalline form to a temperature of 50 to 120° C., under a pressure of 10 to 100 kPa, for 1 to 48 hours.

11. The method according to claim 10, wherein the crystalline form of formula I is the pentahydrate.

12. The method according to claim 10, wherein the crystalline form of formula I is heated to a temperature of 50 to 100° C., at a gradually increasing rate.

13. The method according to claim 11, wherein the pentahydrate of formula I is heated at 110° C. for 18 to 48 hours.

14. The method according to claim 11, wherein said heating is carried out under a reduced pressure of 10 to 30 kPa.

15. A pharmaceutical formulation, comprising the monosodium salt of 3-pyridyl-1-hydroxyethylidene-1,1-bisphosphonic acid in an amorphous form of claim 1 and at least one pharmaceutically acceptable carrier.

16. The pharmaceutical formulation according to claim 15, wherein the carrier is a combination of mannitol and microcrystalline cellulose in tablet form.

17. The pharmaceutical formulation according to claim 15, comprising 5 or 35 mg of the monosodium salt of 3-pyridyl-1-hydroxyethylidene-1,1-bisphosphonic acid in an amorphous form.

18. The monosodium salt of 3-pyridyl-1-hydroxyethylidene-1,1-bisphosphonic acid in an amorphous form according to claim 1, showing a characteristic broad obtuse peak at 2θ angles ranging from 15 to 25° and two sharp peaks at 2θ angles of 5.856 and 6.99°.

19. The monosodium salt of 3-pyridyl-1-hydroxyethylidene-1,1-bisphosphonic acid in an amorphous form, having an X-ray diffraction pattern showing a broad obtuse peak at 2θ angles ranging from 15 to 25°, having bands at 3084, 2936, 1633, 1051 and 120 cm$^{-1}$ in the Raman spectrum, and having expanded bands at 139, 125, 75 and 37 ppm in the $^{13}$C CP MAS NMR spectrum.

* * * * *